United States Patent [19]
Walter

[11] Patent Number: 4,828,548
[45] Date of Patent: May 9, 1989

[54] SAFETY CATHETER

[76] Inventor: Gregory W. Walter, 59 Midwood Rd., West Babylon, N.Y. 11704

[21] Appl. No.: 140,215

[22] Filed: Dec. 31, 1987

Related U.S. Application Data

[63] Continuation-in-part of Ser. No. 26,063, Mar. 16, 1987, Pat. No. 4,772,265.

[51] Int. Cl.⁴ ............................................. A61M 5/00
[52] U.S. Cl. ................................. 604/164; 604/168; 604/143; 604/198
[58] Field of Search ................... 604/164–169, 604/162, 156, 143, 144, 110, 192, 195–198, 263; 128/763–766

[56] References Cited

U.S. PATENT DOCUMENTS

| | | |
|---|---|---|
| Re. 27,797 | 10/1973 | Sorenson et al. .................. 604/162 |
| 3,306,290 | 2/1967 | Weltman . |
| 4,026,287 | 5/1977 | Haller . |
| 4,392,859 | 7/1983 | Dent . |
| 4,507,117 | 3/1985 | Vining et al. . |
| 4,507,118 | 3/1985 | Dent . |
| 4,542,749 | 9/1985 | Caselgrandi et al. . |
| 4,592,744 | 6/1986 | Jagger et al. . |
| 4,676,783 | 6/1987 | Jagger et al. ....................... 604/162 |

Primary Examiner—Dalton L. Truluck
Assistant Examiner—Denise Whelton
Attorney, Agent, or Firm—Leonard Belkin

[57] ABSTRACT

Disposal apparatus for the safe disposal of a medicinal needle after use utilizing a container with a vacuum therein and a piston attached to one side of the needle which protrudes ready for use. After use of the needle, one side of the piston is exposed to ambient pressure and the needle is retracted into the container for safe disposal. A sight chamber attached to said piston within said container and communicating with said needle indicates when said needle has pierced a blood vessel. In another embodiment, a spring is employed to retract the needle.

14 Claims, 2 Drawing Sheets

SAFETY CATHETER

BACKGROUND OF THE INVENTION

This application is a continuation-in-part of my application Ser. No. 026063 filed on Mar. 16, 1987 now U.S. Pat. No. 4,772,265.

The present invention relates to apparatus and method for insuring the safe disposal of hypodermic needles in certain situations and for the prevention of the spread of blood diseases.

When a catheter is inserted into a patient, usually an arm, for the intravenous delivery of a fluid, a disposable needle passing through the catheter is utilized to make the puncture to permit entry of the tip of the catheter. The needle is then withdrawn leaving the catheter in place either for a direct hook-up to the bottle of fluid to be delivered, or capped for later use. The needle, tipped with blood, is dropped into a container for disposal.

It has been found that for needles disposed of in this manner, there is a certain incidence of occurrences in which a hospital technician or other personnel receives a puncture from one of the used needles. With the developing concern over the transmission of AIDS, there is real interest in finding alternative and safer ways of disposing of such needles.

Also noted is that upon withdrawal of the needle from the catheter there is inevitably a certain amount of patient's blood spilled. This blood may harbor certain viral or non-viral diseases and can be the source of exposure for other individuals caring for the patient.

In U.S. Pat. No. 3,306,290 there is taught a syringe containing a spring to retract automatically a needle.

U.S. Pat. No. 4,026,287 discloses a syringe in which the needle is retracted by having a plunger rod rotate to engage the piston attached to the needle so that the latter can be withdrawn in a positive manner.

U.S. Pat. No. 4,392,859 shows an injection gun for use with animals which between injections the needle is put in contact with a sterilizing substance.

U.S. Pat. No. 4,507,117 discloses a syringe in which the plunger makes positive engagement with the needle in the syringe.

U.S. Pat. No. 4,507,118 has an injection gun for use with animals which incorporates a sterilizing element to sterilize the needle between use. A spring is employed to retract the needle each time.

U.S. Pat. No. 4,542,749 teaches a syringe with automatic plunger return relying on either air compressed during injection to return the needle or a separate source of compressed fluid.

U.S. Pat. No. 4,592,744 teaches an arrangement for sheathing a needle after use in which the user of the syringe physically withdraws the latter which grasps and pulls the needle into the sheath.

The arrangements described in the patents above are either too complicated or expensive to be used as disposable items, or require that the user take positive action to effect the safe disposal of the needle, or are not applicable to the particular circumstances to which the present invention pertains.

SUMMARY OF THE INVENTION

This invention overcomes or reduces the disadvantages and drawbacks associated with previous methods and devices designed to reduce the risk of unintended puncture by disposable needles and in addition provides for less exposure to disease.

Briefly described, the present invention embodies a safety catheter assembly having provision to withdraw the needle into a container automatically after use, not requiring that the user of the syringe take any specific extra action to effect the sheathing of the needle. This arrangement avoids the potential of human error and insures that in each and every case of needle use, the needle will be disposed of in a safe manner.

In a preferred embodiment of the invention there is provided a sealed container under a vacuum therein containing a slidable piston. A needle for making the skin puncture to facilitate entry of the intravenous catheter is connected at its proximal end to a blood collection chamber which is in turn connected to the piston, both of which are contained within the sealed container. The needle passes through the catheter to facilitate the insertion of the latter. When the needle is to be removed, the sealed container is separated from the catheter releasing any friction force caused by a rubber seal located at the proximal end of the catheter. Once free of the seal the needle is automatically pulled into the container rendering it incapable of accidentially causing further skin puncture. At the same time the hole in the seal left from the needle is self sealing so that no blood may leak from it.

In another embodiment, a spring may be utilized instead of a vacuum.

It is thus a principal object of this invention to provide a safe method of starting an I.V. with the subsequent safe disposal of medical needles that is also economical.

Other objects and advantages of this invention will hereinafter become obvious from the following description of preferred embodiments of this invention.

DETAILED DESCRIPTION OF THE PREFERRED EMBODIMEMT

Figure 1:
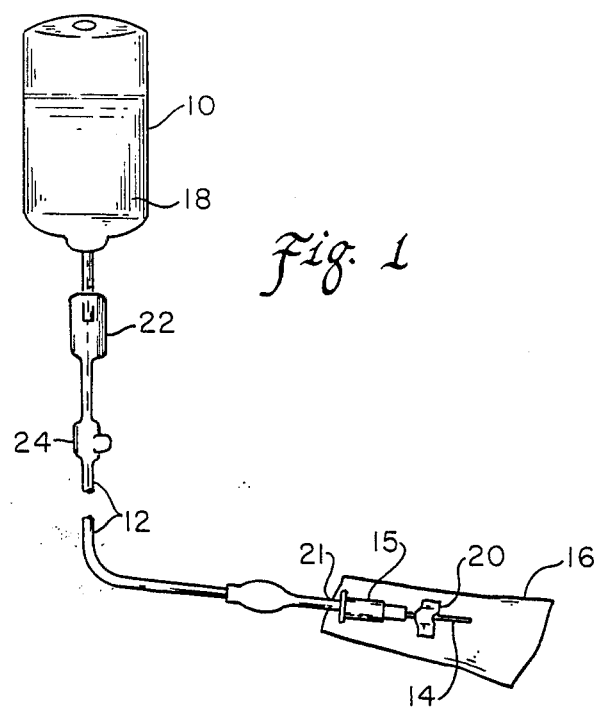
FIG. 1 is a partially schematic view of a conventional I.V. administration system in use.

Referring to FIG. 1, the typical intravenous (I.V.) system consists of reservoir 10 connected through tubing 12 to an intravenous catheter 14 which has been previously inserted into the arm 16 of a patient for the delivery of a parenteral liquid 18 stored in reservoir 10. Tape 20 may be employed to hold catheter 14 in place. Catheter 14 is provided with an adaptor or hub 15 to receive tubing 12 by way of a male adaptor 21.

Tubing 12 is provided with a drip chamber 22 and a flow control valve 24.

Reservoir 10 may be a rigid container which is vented so that air can replace liquid 18 as it drains out or may be a sealed collapsible bag where no venting is required.

Drip chamber 22, being of transparent material, as is understood in the art, performs the primary function of permitting the calculation of flow rate by the counting of drops, although it also may serve to remove any air bubbles which might be present in the liquid.

Flow control valve 24 permits the adjustable clamping of tube 12, and it is used to establish the drip rate at the desired value.

The conventional manner of putting intravenous catheter 14 in place as shown in FIG. 1 is to take catheter 14 which comes with a needle already passing through it with its tip exposed at the distal end of catheter 14 and make the penetration at the injection site. When blood starts dripping out of the backflow chamber of the needle, the needle is withdrawn from catheter 14 leaving the latter in place and adaptor 21 is connected to hub 15, the proximal end of catheter 14. The needle is then discarded, contaminated by blood yet unsheathed, in a container or receptacle labeled to receive such needles for disposal. As noted earlier, with regular frequency, unfortunately, personnel handling the exposed, contaminated needles will suffer injury from the used needles.

Figure 4:
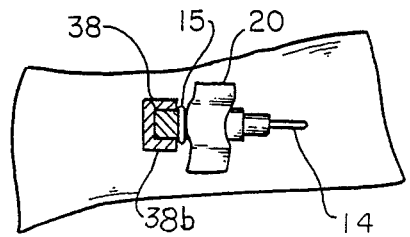
FIG. 4 is an arrangement for intermittent I.V. injections.

Also noted is that, upon withdrawing the needle from catheter 14 there is the possibility of blood flow out of hub 15 if not immediately connected to male I.V. adaptor 21. In this invention, this hazard is avoided totally by an arrangement in which the hub is capped with a seal cover 38b which is designed to prevent leakage of blood, as seen in FIG. 4.

Figure 2:
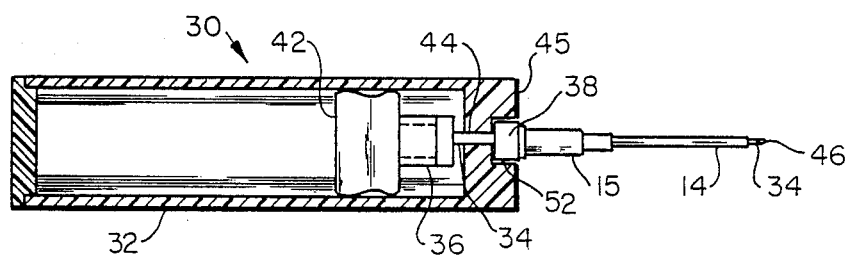
FIG. 2 is a partially schematic view in section through a preferred embodiment of this invention.

Referring to FIG. 2, there is shown a safety catheter assembly 30 embodying the principles of this invention. Catheter assembly 30 consists of a cylindrical container 32, needle 34, blood collection chamber 36 within container 32, and intravenous catheter 14, with a hub 15, on the proximal end of which is mounted seal 38. Assembly 30, except for a protective covering, is illustrated in FIG. 2 in the form it is assembled and delivered and ready for use.

Cylindrical container 32 is a sealed unit containing a rubber piston 42 at one end to which is attached on its right side as shown sight chamber 36 which receives and is attached to the proximal end of needle 34 which extends out of container 32, passing through a port 44 in end wall 45 of container 32, and through catheter 14 terminating with its tip 46 exposed for use. Container 32 is under a negative pressure, that is there as a partial vacuum within. The right end of container 32 is provided with a countersunk depression 52 to accommodate rubber seal 38 that caps catheter hub 15 and seals port 44. Seal 38 has an opening 38a to permit passage therethrough of needle 34. Opening 38a is filled with a sealant for a purpose to be described below. The proximal end of needle 34 opens into sight chamber 36. The walls of chamber 32 are made of transparent material, such as any suitable plastic, so that sight chamber 36 can be viewed for the deposit of blood out of needle 34.

Figure 3:
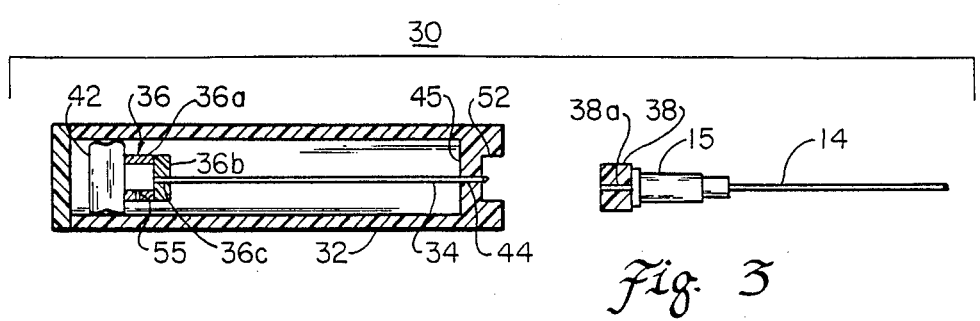
FIG. 3 is an exploded view in partial section of the apparatus shown in FIG. 2 after the needle has retracted.

Blood collection chamber 36, as also seen in FIG. 3, consists of a hollow cylinder 36a of transparent material attached to rubber piston 42 on the left as noted and vented through an opening 55. On the opposite end, chamber 36 is attached to and communicates with the interior of needle 34 as previously noted. As a result of opening 55, there is a vacuum to the left of piston 42, while there is ambient pressure on the right side. Opening 38a in seal 38 with sealant in contact with needle 34 provides sufficient resistance to prevent piston 42 from moving to the left under the force of ambient pressure.

Needle 34 passes through port 44, passageway 38a in seal 38, hub 15 and catheter 14, as shown in FIG. 2.

As has already been noted, blood collection chamber 36 is clearly visible through container 32 (see FIG. 2) so that when needle 34 enters the patient's arm to install catheter 14, blood emptying from its proximal end into sight chamber 36 confirms that a blood vessel has been pierced.

In the use of the apparatus shown in FIG. 2, the professional or technician uses assembly 30 in a conventional manner to place catheter 14 in the arm or other suitable location in the patient. When blood return is visible in blood collection chamber 36 it confirms that the blood vessel has been entered and the distal end of the catheter 14 is located properly, then catheter hub 15 is partially separated from container 32. That is, the professional or technician grasps hub 15 stabilizing it against the patients arm as he pulls it away from container 32. This retracts needle tip 46 into catheter 14 preventing it from further lacerating the already entered vein. Catheter 14 may now be completely advanced into the vein as is the common manner of placement. Once catheter 14 is properly positioned in a vein, container 32 is completely removed from hub 15 and seal 38 thereby removing friction from seal 38 in passageway 38a on needle 34. This results in piston 42, collection chamber 36 and needle 34 automatically retracting into container 32 due to the ambient pressure on the right side of piston 42 and a vacuum on its left side. Rubber seal 38 remains attached to hub 15 and catheter 14 upon removal of needle 34, opening 38a closes off, preventing any leakage of blood, due to the use of a sealant within passageway 38a. Such sealants are presently commercially available and are generally used for sealing openings after a needle has been withdrawn. If desired, it may be modified with an outer rim composed of threads or tabs (not shown) to facilitate its connection with intravenous delivery tubing.

Figure 5:
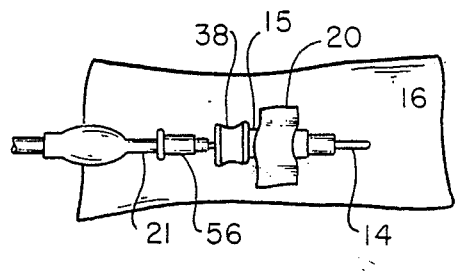
FIG. 5 and 6 show alternative arrangements for employing the invention for continuous infusion.

Hub 15 would remain in place mounted on catheter 14 and may be utilized in certain ways. For example, as seen in FIG. 5, catheter 14 may be retained in place by tape 20. In this way, the arrangement may be utilized for intermittent injection, that is, seal 38 and hub 15 pierced with an injection needle 56 to administer medication not required continously. The catheter would then be periodically flushed with a solution to prevent blood clotting in it.

Figure 6:
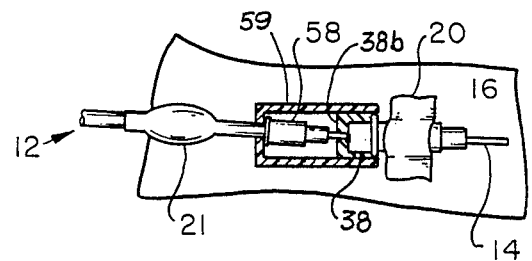

Another way to utilize hub 15 is shown in FIG. 6 where a needle 58 connected to a constant I.V. delivery source is inserted into seal 38 and hub 15, all within an enclosure 59. This can be accomplished in a conventional manner using a standardly available hypodermic needle as shown in FIG. 5 or using a needle modified to prevent its exposure as in FIG. 6.

Except for the needle, piston 42, and seal 38 which are made out of metal and rubber respectively, assembly 30 could be constructed out of plastic and therefore inexpensive to manufacture.

Figure 7:
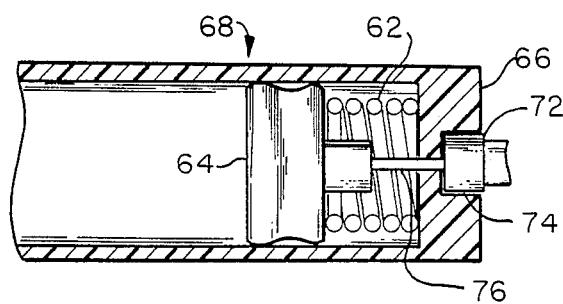
FIG. 7 is a partial view in section of an alternative embodiment of this invention.

Instead of using a vacuum to actuate piston 42, as seen in FIG. 7, a spring 62 mounted between piston 64 and end wall 66 of container 68 may be utilized to drive piston 64 to the left after seal 72 is detached from recess 74.

In this arrangement, with needle 76 penetrating seal 72 there is sufficient resistance to prevent piston 64 from retracting needle 76. However, upon separation of seal 72 as described in the embodiment of FIGS. 1–3, needle 76 is freed from seal 72 and spring 62 exerts sufficient pressure on piston 64 to cause its movement to the left and the retraction of needle 76 into container 68.

In the embodiments described, it is seen that there have been provided arrangements which insure the safe disposal of a needle after use without requiring extra specific steps to be taken by the user of the equipment.

While only preferred embodiments of the invention have been described, it is understood that many changes are possible without departing from the principles of this invention as defined in the claims which follow.

What is claimed is:

1. Apparatus for the safe disposal of a medical needle comprising:
   a. container means containing slidable piston means;
   b. sight chamber means mounted on one side of said piston means;
   c. said needle attached at its proximal end to said sight chamber means and communicating with the interior of said chamber, said needle extending out of said container means;
   d. hollow catheter means outside of said container means having said needle passing therethrough for the penetration of a blood vessel of a patient to facilitate insertion of the distal end of said catheter means;
   e. sealing means mounted on the proximal end of said catheter means for removably attaching said catheter means to said container means so that said needle extends through said sealing means into said catheter means and out of the distal end of said scatheter means; and
   f. means within said container means for driving said piston means in the direction of retracting said needle into said container means, said sealing means including means for preventing said piston means from being retracted and upon separation of said sealing means from said container means after use of said needle releasing said piston means to permit retraction of said piston means whereby said needle is safely sheathed for disposal after use.

2. The apparatus of claim 1 in which said sealing means has an opening through which said needle passes, said opening including means for sealing said opening upon said needle being retracted.

3. The apparatus of claim 2 wherein said container means is constructed of a transparent wall whereby said sight chamber is visible.

4. The apparatus of claim 3 in which said container means with needle, sealing means, and catheter means come assembled as a sterile unit available for the insertion of said catheter means into said patient.

5. The apparatus of claim 3 wherein said sight chamber includes venting means for maintaining a pressure within not in excess of ambient for confirming that a blood vessel has been pierced by said needle.

6. The apparatus of claim 1 in which said container means is under a vacuum therein on the side of said piston means away from said sealing means, said sealing means upon separation form said container means exposing said piston means to ambient pressure on the side to which said needle is attached.

7. The apparatus of claim 1 in which said means to drive said piston means comprises spring means, said sealing means in contact with said container means preventing said piston means from being moved by said spring means.

8. A sterile and disposable apparatus for the safe disposition of a medicinal needle used in connection with a catheter for insertion of the latter into the blood vessel of a patient, said apparatus comprising an assembly of:
   a. A medicinal needle and container means for enclosing the proximal end of said needle, said needle protruding from said container means;
   b. a hollow catheter for receiving said needle with the tip of the latter protruding from the distal end of said catheter and ready for use;
   c. means for releasably engaging the proximal end of said catheter to said container means through which said needle passes; and
   d. retracting means in said container means upon disengagement of said engaging means from said container means after use of said needle to cause said needle to retract into said container means for disposal, said engaging means preventing said needle from being retracted while engaged to said container means.

9. The apparatus of claim 8 in which said container means includes a sight chamber and the proximal end of said needle communicates with the interior of said sight chamber.

10. The apparatus of claim 9 wherein said engaging means is attached to the end of catheter means to receive said needle and includes means to seal said catheter means against leakage of blood when said engaging means is released from said container means and said needle is retracted into said container means.

11. The apparatus of claim 10 wherein said container means contains a vacuum therein and piston means at one end thereof attached to the proximal end of said needle through said sight chamber, said engaging means upon being disengaged from said container means releasing said piston means to permit ambient pressure to drive said piston means in the direction of pulling said needle into said container means.

12. The method of safely disposing of a medicinal needle comprising the steps of attaching the proximal end of said needle to a sight chamber mounted on one side of a piston within a sealed container, said container having means to drive said piston to the other side of said container, said needle communicating with said sight chamber and extending out of said container prepared for use, and said container including means for preventing movement of said piston followed by the step of releasing said piston after use of said needle to permit said piston to move and retract said needle into said container whereby said needle is safely sheathed.

13. The method of claim 12 wherein said container includes sealing means and is under vacuum and said needle prior to use passses through said sealing means, said sealing means including a seal which is destroyed by the step of separating said sealing means from said container after use of said needle, thereby permitting said piston under ambient pressure on one side to cause movement of said piston in the direction of retracting said needle into said container.

14. The method of claim 12 wherein said drive means comprises spring means and release of said piston permits said spring means to drive said piston to retract said needle.

* * * * *